United States Patent [19]

Rasmussen

[11] Patent Number: 5,075,315

[45] Date of Patent: Dec. 24, 1991

[54] ANTIPSYCHOTIC HEXAHYDRO-2H-INDENO[1,2-C]PYRIDINE DERIVATIVES

[75] Inventor: Chris R. Rasmussen, Lansdale, Pa.

[73] Assignee: McNeilab, Inc., Spring House, Pa.

[21] Appl. No.: 524,604

[22] Filed: May 17, 1990

[51] Int. Cl.$^5$ .................. C07D 519/00; A61K 31/505
[52] U.S. Cl. ..................................... 514/266; 514/267; 544/54; 544/263; 544/278; 544/281; 544/282; 544/321
[58] Field of Search ............... 544/321, 278, 281, 282, 544/263, 54; 514/266, 267

[56] References Cited

U.S. PATENT DOCUMENTS

| 3,678,057 | 7/1972 | Ebnother et al. .................... 544/242 |
| 4,957,916 | 9/1990 | Kennis ................................ 514/254 |

FOREIGN PATENT DOCUMENTS

| 472407 | 3/1969 | European Pat. Off. ............ 544/242 |
| 749919 | 4/1970 | European Pat. Off. ............ 544/242 |
| 527195 | 8/1972 | European Pat. Off. ............ 544/242 |
| 3002367 | 1/1980 | European Pat. Off. ............ 544/242 |
| 867249 | 11/1989 | European Pat. Off. ............ 544/242 |
| 378255 | 7/1990 | European Pat. Off. ............ 544/3 X |
| 53-012426 | 2/1978 | Japan .................................. 544/242 |

OTHER PUBLICATIONS

Journal of Medicinal Chemistry—15(5), 466–470 (1972) Relationship between Antihistamine and Antidepressant Activity in Hexahydroindenopyridines.
Mutat. Res., 66(2), 113–127 (1979)—Actions of an Antispermatogenic, but Non-Mutagenic, Indenopyridine Derivative in Mice and Salmonella typhimurium.
J. Med Chem., 23, 949–952 (1980) hexahydrophyrido[4-,3-b]indoles useful as neuroleptics.
J. Med. Chem., 29 8–19 (1986) Neuroleptic Activity of Chiral trans-Hexahydro-y-carbolines.

Primary Examiner—Robert Gerstl
Attorney, Agent, or Firm—Charles J. Metz

[57] ABSTRACT

Novel hexahydro-2H-indeno[1,2-c]pyridines and their pharmaceutically acceptable acid addition salts having useful antipsychotic properties.

6 Claims, No Drawings

ANTIPSYCHOTIC HEXAHYDRO-2H-INDENO[1,2-C]PYRIDINE DERIVATIVES

BACKGROUND OF THE INVENTION

In U.S. Pat. No. 3,678,057 there are described hexahydro-indenopyridines having serotonin-antagonistic, antiphlogistic and analgesic activities. BE-749,919 describes hexahydro-indenopyridines useful as serotonin antagonists. In CH-527,195 there are described hexahydro-indenopyridines having serotonin-antagonistic and analgetic activities. The Journal of Medicinal Chemistry, 15(5), 466–470 (1972) describes the relationship between antihistamine and antidepressant activity in hexahydro indenopyridines.

The compounds of the present invention differ from the cited hexahydro-indenopyridines by the fact that they are substituted with a pyrimidinone moiety in a previously undisclosed manner and particularly by their favourable antipsychotic properties.

DESCRIPTION OF THE INVENTION

The present invention is concerned with novel hexahydro-2H-indeno[1,2-c]pyridines having the formula:

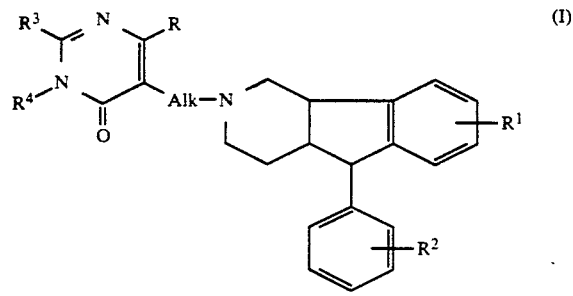

the pharmaceutically acceptable acid addition salts and stereochemically isomeric forms thereof,
wherein
R represents hydrogen or $C_{1-6}$alkyl;
$R^1$ and $R^2$ each independently represent hydrogen, halo, hydroxy, $C_{1-6}$alkyloxy, $C_{1-6}$alkyl, trifluoromethyl, mercapto or $C_{1-6}$alkylthio; and
$R^3$ represents $NR^5R^6$ wherein:
  $R^5$ represents hydrogen or $C_{1-6}$alkyl; and
  $R^6$ represents hydrogen, $C_{1-6}$alkyl, aryl$C_{1-6}$alkyl or $C_{1-6}$alkylcarbonyl;
$R^4$ represents hydrogen or $C_{1-6}$alkyl; or
$R^3$ and $R^4$ taken together may form a bivalent radical of formula -Z-A- wherein:
  Z is —S—, —$NR^5$—, —$CR^7$=$CR^8$— or —$CH_2$— wherein in the latter one hydrogen atom may be replaced by hydroxy or $C_{1-6}$alkyl and $R^5$ is as defined above and $R^7$ and $R^8$ each independently represent hydrogen or $C_{1-6}$alkyl;
  A is a bivalent radical —$CR^9$=$CR^{10}$—, —$CH_2$—$CH_2$— or —$CH_2$—$CH_2$—$CH_2$— wherein in the latter two radicals one or two hydrogen atoms may be replaced by $C_{1-6}$alkyl; and $R^9$ and $R^{10}$ each independently represent hydrogen or $C_{1-6}$alkyl; or when Z is —S— or —$NR^5$—, then A may also be —$CR^{11}$=N—, wherein $R^{11}$ represents hydrogen, $C_{1-6}$alkyl or trifluoromethyl;
Alk represents $C_{1-4}$alkanediyl; and
each aryl independently is phenyl optionally substituted with 1,2 or 3 substituents each independently selected from halo, $C_{1-6}$alkyl, trifluoromethyl, $C_{1-6}$alkyloxy and hydroxy.

In the foregoing definitions the term halo defines fluoro, chloro, bromo and iodo; $C_{1-6}$alkyl defines straight and branch chained saturated hydrocarbon radicals, having from 1 to 6 carbon atoms, such as, for example, methyl, ethyl, 1-methylethyl, 1,1-dimethylethyl, propyl, butyl, pentyl, hexyl and the like; and $C_{1-4}$alkanediyl defines bivalent straight or branch chained alkanediyl radicals having from 1 to 4 carbon atoms, such as, for example, methylene, 1,2-ethanediyl, 1,3-propanediyl, 1,4-butanediyl and the branched isomers thereof.

The compounds of formula (I) wherein $R^5$, $R^6$ and/or $R^4$ are hydrogen may also occur as tautomeric forms. Such forms, although not explicitly indicated in the above formula are intended to be included within the scope of the present invention.

Said acid addition salts as mentioned hereinabove are meant to comprise the therapeutically active, and in particular, pharmaceutically acceptable, non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like, sulfuric acid, nitric acid, phosphoric acid and the like; or organic acids, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form. The term acid addition salt also comprises the hydrates and solvent addition forms which the compounds of formula (I) are able to form. Examples of such forms are e.g. hydrates, alcoholates and the like.

Because of different annelation possibilities between the piperidine and cyclopentene ring in the tricyclic ring system, and depending on the relative position of the phenyl substituent on the cyclopentene ring, the compounds of formula (I) may occur in cis/trans isomeric forms. Alternatively, such isomeric forms can be denoted by the descriptors α and β which define the relative position of the ring substituents. The cis/trans and α/β descriptors herein referred to are used in accordance with the rules described in Chem. Abstr. 1977 Index Guide, Appendix IV, § 203.

The compounds of formula (I) have at least three asymmetric carbon atoms, namely those located in the 4a-, 5- and 9b-position of the tricyclic moiety and may therefore occur as stereochemically isomeric forms. Stereochemically isomeric forms as well as cis/trans isomeric forms, as well as mixtures thereof, are obviously intended to be embraced within the scope of the invention.

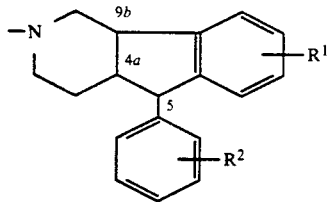

Particular compounds are those compounds of formula (I) wherein -Z-A- may be —S—CH$_2$—CH$_2$—, —S—CH$_2$—CH$_2$—CH$_2$—, —S—CH=CH—, —S—CH=C(CH$_3$)—, —S—C(CH$_3$)=N—, —S—C(CF$_3$)=N—, —N(CH$_3$)—CH$_2$—CH$_2$—, —N(CH$_3$)—CH$_2$—CH$_2$—CH$_2$—, —N(CH$_3$)—CH=CH—, —N(CH$_3$)—CH=C(CH$_3$)—, —N(CH$_3$)—C(CH$_3$)=N—, —CH=CH—CH=CH—, —C(CH$_3$)=CH—CH=CH—, —CH=CH—C(CH$_3$)=CH—, —CH$_2$—CH$_2$—CH$_2$—CH$_2$—, —CHOH—CH$_2$—CH$_2$—CH$_2$—, —CH(CH$_3$)—CH$_2$—CH$_2$—CH$_2$—, —CH$_2$—CH$_2$—CH(CH$_3$)—CH$_2$— or —CH(CH$_3$)—CH$_2$—CH(CH$_3$)—CH$_2$—.

Preferred are those particular compounds wherein R is C$_{1-6}$alkyl; and/or R$^1$ and R$^2$ are both halo; and/or -Z-A- is —S—CH$_2$—CH$_2$—, —S—CH$_2$—CH$_2$—CH$_2$—, —S—CH=CH—, —S—C(CH$_3$)=N—, —S—C(CF$_3$)=N—, —N(CH$_3$)—CH$_2$—CH$_2$—, —N(CH$_3$)—CH=CH—, —CH=CH—CH=CH—, —CH$_2$—CH$_2$—CH$_2$—CH$_2$— or —CH$_2$—CH$_2$—C(CH$_3$)—CH$_2$—.

More preferred are those groups of compounds as defined above or hereinafter wherein the configuration between the 9b and 4a hydrogen atoms as well as between the 4a and 5 hydrogen atoms is trans; or in terms of α and β, that the hydrogen atom of 4a is in α-position, that of 9b in β-position and the aryl group in α-position (i.e. 4aα,5α,9bβ).

Particularly preferred compounds are those more preferred compounds wherein R is methyl, R$^1$ is 8-fluoro, R$^2$ is 4-fluoro, and -Z-A- is —S—CH$_2$—CH$_2$—, —S—CH=CH—, —N(CH$_3$)—CH$_2$—CH$_2$—, —N(CH$_3$)—CH=CH—, —CH=CH—CH=CH—, —CH$_2$—CH$_2$—CH$_2$—CH$_2$— or —CH$_2$—CH$_2$—C(CH$_3$)—CH$_2$—.

The most preferred compounds are selected from the group consisting of (−)-(4aα,5α,9bβ)-3-[2-[8-fluoro-5-(4-fluorophenyl)-1,3,4,4a,5,9b-hexahydro-2H-indeno[1,2-c]pyridin-2-yl]ethyl]-6,7,8,9-tetrahydro-2-methyl-4H-pyrido[1,2-a]pyrimidin-4-one, the stereoisomers and the pharmaceutically acceptable acid addition salts thereof.

In order to simplify the structural representations of the compounds of formula (I) and of certain starting materials and intermediates thereof, the radical

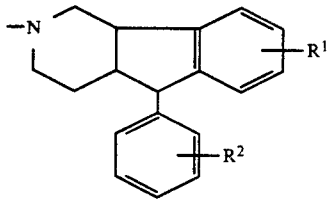

will hereafter be represented by the symbol D.

The compounds of formula (I) can generally be prepared by N-alkylating an intermediate of formula (II) with a pyrimidinone of formula (III) following art-known N-alkylation procedures.

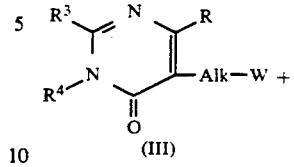

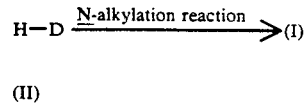

In formula (III) W represents an appropriate reactive leaving group such as, for example, halo, e.g. chloro, bromo or iodo; sulfonyloxy, e.g. methanesulfonyloxy, trifluoromethanesulfonyloxy, benzenesulfonyloxy, 4-methylbenzenesulfonyloxy and the like leaving groups. Said N-alkylation reaction can conveniently be carried out by mixing the reactants, optionally in a reaction-inert solvent such as, for example, water; and aromatic solvent, e.g. benzene, methylbenzene, dimethylbenzene, chlorobenzene, methoxybenzene and the like; a C$_{1-6}$alkanol, e.g. methanol, ethanol, 1-butanol and the like; a ketone, e.g. 2-propanone, 4-methyl-2-pentanone and the like; an ester, e.g. ethyl acetate, γ-butyrolactone and the like; an ether, e.g. 1,1'-oxybisethane, tetrahydrofuran, 1,4-dioxane and the like; a dipolar aprotic solvent, e.g. N,N-dimethylformamide, N,N-dimethylacetamide, dimethylsulfoxide, pyridine, 1,3-dimethyl-3,4,5,6-tetrahydro-2(1H)-pyrimidinone, 1,3-dimethyl-2-imidazolidinone, 1,1,3,3-tetramethylurea, 1-methyl-2-pyrrolidinone, nitrobenzene, acetonitrile and the like; or a mixture of such solvents. The addition of an appropriate base such as, for example, an alkali metal or an alkaline earth metal carbonate, hydrogen carbonate, hydroxide, oxide, carboxylate, alkoxide, hydride or amide, e.g. sodium carbonate, sodium hydrogen carbonate, potassium carbonate, sodium hydroxide, calcium oxide, sodium acetate, sodium methoxide, sodium hydride, sodium amide and the like, or an organic base such as, for example, a tertiary amine, e.g. N,N-diethylethanamine, N-ethyl-N-(1-methylethyl)-2-propanamine, 4-ethylmorpholine, 1,4-diazabicyclo[2.2.2]octane, pyridine and the like, may optionally be used to pick up the acid which is formed during the course of the reaction. In some instances the addition of an iodide salt, preferably an alkali metal iodide, or a crown ether, e.g. 1,4,7,10,13,16-hexaoxacyclooctadecane and the like, may be appropriate. Stirring and somewhat elevated temperatures may enhance the rate of the reaction; more in particular the reaction may be conducted at the reflux temperature of the reaction mixture. Additionally, it may be advantageous to conduct said N-alkylation under an inert atmosphere such as, for example, oxygen-free argon or nitrogen gas.

Alternatively, said N-alkylation may be carried out by applying art-known conditions of phase transfer catalysis reactions. Said conditions comprise stirring the reactants, with an appropriate base and optionally under an inert atmosphere as defined hereinabove, in the presence of a suitable phase transfer catalyst such as, for example, a trialkylphenylmethylammonium, tetraalkylammonium, tetraalkylphosphonium, tetraarylphosphonium halide, hydroxide, hydrogen sulfate and the like catalysts. Somewhat elevated temperatures may be appropriate to enhance the rate of the reaction.

The compounds of formula (I) can alternatively be prepared following art-known reductive N-alkylation reaction procedures of an intermediate of formula (II) with an appropriate aldehyde of formula (IV).

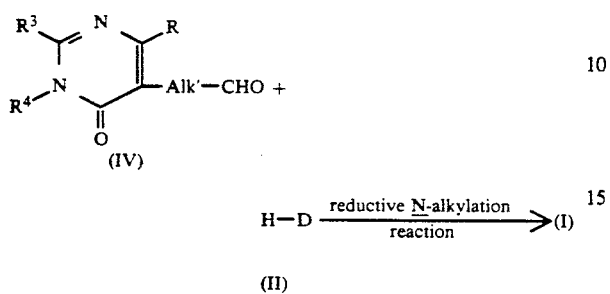

Alk' has the same meaning as Alk, with the proviso that one methylene is lacking. Said reductive N-alkylation reaction may conveniently be carried out by reducing a mixture of the reactants in a suitable reaction-inert solvent. In particular, the reaction mixture may be stirred and/or heated in order to enhance the reaction rate. Suitable solvents are, for example, water; $C_{1-6}$alkanols, e.g. methanol, ethanol, 2-propanol and the like; esters, e.g. ethyl acetate, γ-butyrolactone and the like; ethers, e.g. 1,4-dioxane, tetrahydrofuran, 1,1'oxybisethane, 2-methoxyethanol and the like; halogenated hydrocarbons, e.g. dichloromethane, trichloromethane and the like; dipolar aprotic solvents, e.g. N,N-dimethylformamide, dimethyl sulfoxide and the like; carboxylic acids, e.g. acetic acid, propanoic acid and the like; or a mixture of such solvents. The term "art-known reductive N-alkylation procedures" means that the reaction is carried out either with sodium cyanoborohydride, sodium borohydride, formic acid or a salt thereof, e.g. ammonium formate and the like reducing agents, or alternatively under hydrogen atmosphere, optionally at an increased temperature and/or pressure, in the presence of an appropriate catalyst such as, for example, palladium-on-charcoal, platinum-on-charcoal and the like. In order to prevent the undesired further hydrogenation of certain functional groups in the reactants and the reaction products, it may be advantageous to add an appropriate catalyst-poison to the reaction mixture, e.g., thiophene, quinoline-sulphur and the like. In some instances it may also be advantageous to add an alkali metal salt to the reaction mixture such as, for example, potassium fluoride, potassium acetate and the like salts.

The compounds of formula (I), wherein $R^3$ and $R^4$ taken together form a radical of formula -Z-A-, said compounds being represented by formula (I-a), can be prepared following art-known cyclization procedures for preparing pyrimidin-4-ones such as, for example, by reacting an amidine of formula (V) with a β-dicarbonyl intermediate of formula (VI), or by cyclizing a reagent of formula (VII) with an enamine of formula (VIII).

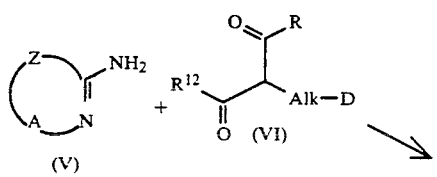

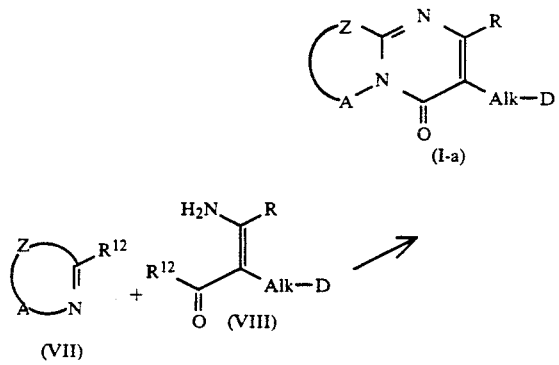

Each $R^{12}$ independently represents an appropriate leaving group such as, for example, $C_{1-6}$alkyloxy, hydroxy, halo, amino, mono- and di($C_{1-6}$alkyl)amino and the like.

Said cyclization reactions may generally be carried out by stirring the reactants, optionally in the presence of a suitable reaction-inert solvent such as, for example, an aliphatic, alicyclic or aromatic hydrocarbon, e.g. hexane, cyclohexane, benzene and the like; pyridine, N,N-dimethylformamide and the like dipolar aprotic solvents. In order to enhance the rate of the reaction it may be appropriate to increase the temperature, more particularly, it may be recommendable to carry out the reaction at the reflux temperature of the reaction mixture.

Following the same cyclization procedures, the compounds of formula (I-a) can also be prepared by cyclizing an intermediate of formula (VIII) with a reagent of formula (IX).

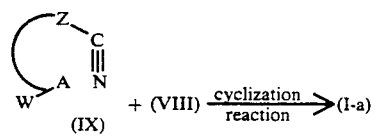

The compounds of formula (I-a) wherein Z is S and A is —$CH_2$—$CH_2$— or —$CH_2$—$CH_2$—$CH_2$—, each of the latter radicals being optionally substituted with one or two $C_{1-6}$alkyl groups, said compounds being represented by the formula (I-a-1)and (I-a-2) respectively, can also be prepared by cyclizing a 2-mercaptopyrimidinone of formula (X) with a reagent of formula (XI), wherein each W independently has the same meaning as previously described and n is 2 or 3.

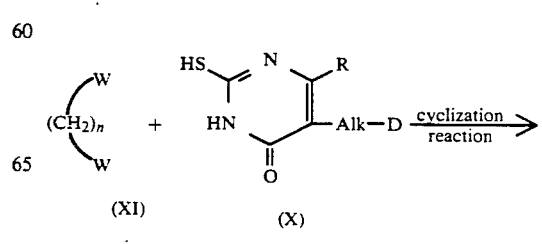

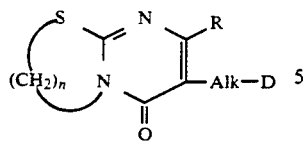

(I-a-1; n = 2)
(I-a-2; n = 3)

The compounds of formula (I-a) wherein Z is S and A is —CR$^9$=CR$^{10}$— said compounds being represented by the formula (I-a-3), can be prepared by cyclizing a 2-mercaptopyrimidinone of formula (X) with a reagent of formula (XII).

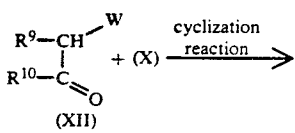

(XII)

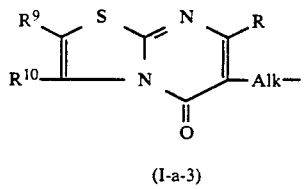

(I-a-3)

The cyclization reactions for preparing the compounds of formulae (I-a-1), (I-a-2) and (I-a-3) may generally be carried out by stirring the reactants together, if desired, in the presence of a suitable reaction-inert solvent such as, for example, an aliphatic, alicyclic or aromatic hydrocarbon, e.g., hexane, cyclohexane, benzene and the like; pyridine; N,N-dimethylformamide and the like dipolar aprotic solvents. Elevated temperatures may be appropriate to enhance the reaction rate. In some cases it may be preferable to carry out the reaction at the reflux temperature of the reaction mixture.

The compounds of formula (I-a) wherein Z is NR$^5$ and A is —CH$_2$—CH$_2$— or —CH$_2$—CH$_2$—CH$_2$—, said compounds being represented by (I-a-4) or (I-a-5), can also be prepared by condensing an alkylating agent (XI) with a compound of formula (I) wherein R$^3$ is NHR$^5$ and R$^4$ is hydrogen, said compound being represented by formula (I-b-1). For example the N-alkylation reaction of compound (I-b-1), with a 1,2-dihaloethane or a 1,3-dihalopropane yields the compounds of formula (I-a-4) or (I-a-5).

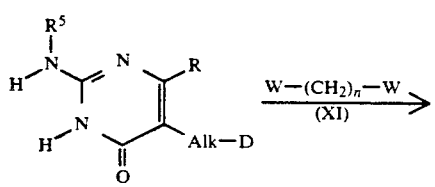

(I-b-1)

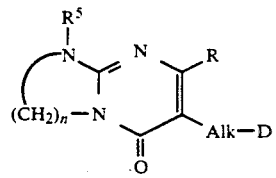

(I-a-4; n = 2)
(I-a-5; n = 3)

Said cyclization reaction can be carried out in a suitable reaction-inert solvent such as, for example, a hydrocarbon, e.g. methylbenzene, ethylbenzene and the like; a dipolar aprotic solvent, e.g. N,N-dimethylformamide, dimethyl sulfoxide, benzonitrile and the like. Also, the addition of an appropriate base such as, for example, an alkali or alkaline earth metal carbonate, hydrogen carbonate or hydroxide and the like, e.g. sodium carbonate, sodium hydrogen carbonate, potassium carbonate and the like, may be utilized to pick up the acid which is liberated during the course of the reaction.

Compounds of formula (I-a) wherein Z is NR$^5$ and A is —CR$^9$=CR$^{10}$—, said compounds being represented by (I-a-6) can be obtained by condensing (I-b-1) with a α-haloketone or -aldehyde (XIII) in a suitable reaction-inert solvent and in the presence of an appropriate acid or base. Suitable reaction-inert solvents are, for example, hydrocarbons, e.g. methylbenzene, ethylbenzene and the like; dipolar aprotic solvents, e.g. N,N-dimethylformamide, dimethyl sulfoxide, benzonitrile and the like.

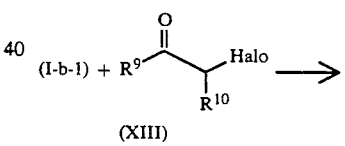

(XIII)

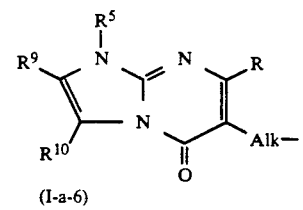

(I-a-6)

The 2-aminopyrimidinones of formula (I-b) can be prepared from an appropriate mercaptopyrimidinone (X-a), by S-alkylating it first to an alkylthio intermediate of formula (XIV) and subsequently substituting this alkylthio substituent with an amine HNR$^5$R$^6$.

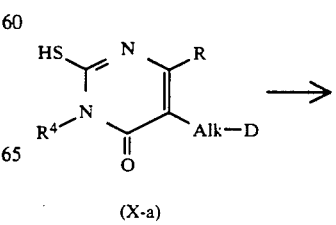

(X-a)

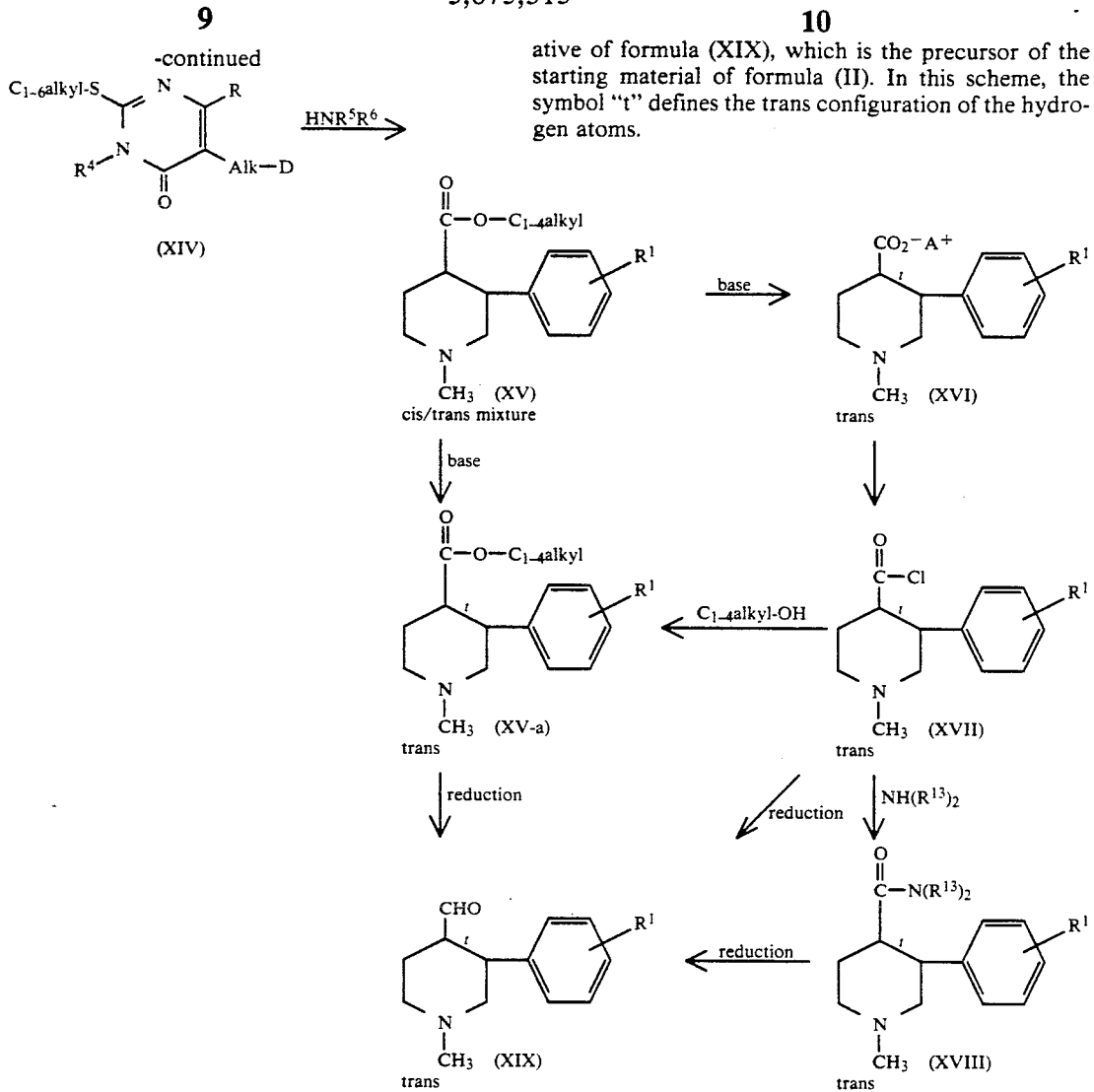

(XIV)

ative of formula (XIX), which is the precursor of the starting material of formula (II). In this scheme, the symbol "t" defines the trans configuration of the hydrogen atoms.

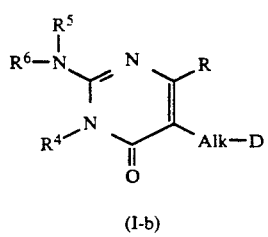

(I-b)

A number of intermediates and starting materials in the foregoing preparations are known compounds which may be prepared according to art-known methodologies of preparing said or similar compounds. For example some of the intermediates of formula (III) and their preparations are described in U.S. Pat. No. 4,804,663, and in the references cited therein. Other intermediates may be prepared according to art-known methodologies of preparing similar compounds and for some of them, preparative methods are presented hereinafter. In the next reaction scheme there are described different routes to prepare the 4-formylpiperidine deriv- A cis/trans mixture of 4-piperidinyl-ester of formula (XV), which is prepared according to procedures as described in U.S. Pat. No. 3,678,057, can be epimerized to the trans isomer of formula (XV-a), in the presence of an appropriate base, such as an alkali metal alkoxide, e.g. sodium methoxide, sodium ethoxide, potassium ethoxide and the like, in a suitable organic solvent such as methanol, ethanol and the like. The cis/trans mixture of the ester of formula (XV) can also be converted into the corresponding salt form of formula (XVI) with an appropriate base such as an alkali metal hydroxide, e.g. sodium hydroxide, potassium hydroxide and the like, in a suitable reaction-inert solvent such as an alcohol, e.g. methanol, ethanol or 2-propanol. In formula (XVI) $A^+$ represents a counter ion such as an alkali metal cation. During the alkaline hydrolysis of (XV) to (XVI), most or all of the cis isomeric form epimerizes to the trans isomeric form. In the above reactions, in order to enhance the reaction rate, it may be appropriate to heat the reaction mixture.

The salt of formula (XVI) is converted into the corresponding acylchloride of formula (XVII) with a halogenating reagent such as thionyl chloride, phosphorus pentachloride, phosphorus trichloride or phosphorus oxychloride, optionally in a suitable reaction-inert solvent. Suitable solvents comprise aliphatic hydrocarbons, e.g. hexane, heptane and the like; aromatic hydrocarbons, e.g. benzene, methylbenzene and the like; halogenated hydrocarbons, e.g. dichloromethane, trichloromethane and the like.

The acylchloride of formula (XVII) can be converted to the ester of formula (XV-a) by treatment with a $C_{1-4}$alkanol, if necessary in a suitable reaction-inert solvent.

The 4-formylpiperidine derivative of formula (XIX) may be prepared in three different ways. First from the ester derivative of formula (XV-a) by reduction with, for example, DIBAL in a suitable reaction-inert solvent such as an ether, e.g. 1,1-oxybisethane, tetrahydrofuran or dioxane.

Secondly, (XIX) can be obtained by reduction of the acylchloride derivative of formula (XVII) in the presence of hydrogen and an appropriate catalyst such as palladium-on-charcoal, platinum-on-charcoal in a suitable reaction-inert solvent. It may be appropriate to add a catalyst poison such as sulfur or thiophene to the reaction mixture (Rosenmund reduction). Reaction-inert solvents for use in said reduction comprise aliphatic or aromatic hydrocarbons such as, for example, hexane, heptane, benzene, methylbenzene and the like. The reduction reaction may also be carried out with $LiAlH[OC(CH_3)_3]_3$ as reducing agent in a reaction-inert solvent such as an ether, e.g. 1,4-dioxane, 1,2-dimethoxyethane, 1,1'-oxybis(2-methoxyethane) and the like.

Finally, the 4-formylpiperidine (XIX) can be prepared in a two step procedure from the acyl chloride of formula (XVII) upon treatment with an amine $NH(R^{13})_2$, to form an amide of formula (XVIII), wherein $R^{13}$ represents $C_{1-4}$alkyl or both $R^{13}$ taken together form $-(CH_2)_4-$, $-(CH_2)_5-$ or $-(CH_2)_2-O-(CH_2)_2-$. This reaction can be carried out in a reaction-inert solvent such as an aliphatic or aromatic hydrocarbon, e.g. pentane, hexane, heptane, benzene, methylbenzene and the like; a halogenated hydrocarbon, e.g. dichloromethane, trichloromethane, 1,2-dichloroethane and the like. The amide derivative of formula (XVIII) in turn is reduced to a 4-formylpiperidine (XIX) by procedures which employ selective reducing agents for conversion of amides to aldehydes such as, for example, $LiAlH(OC_2H_5)_3$ in a suitable inert solvents such as 1,1'-oxybisethane, tetrahydrofuran, dioxane, and the like for the preparation of (XIX) from (XVIII). Any cis isomer which may be formed in the course of this procedure may optionally be removed by art-known separation techniques.

The next reaction scheme describes the preparation of the starting materials of formula (II). The symbol "t" defines the trans configuration of the 9b and 4a as well as the 4a and 5 hydrogen atoms.

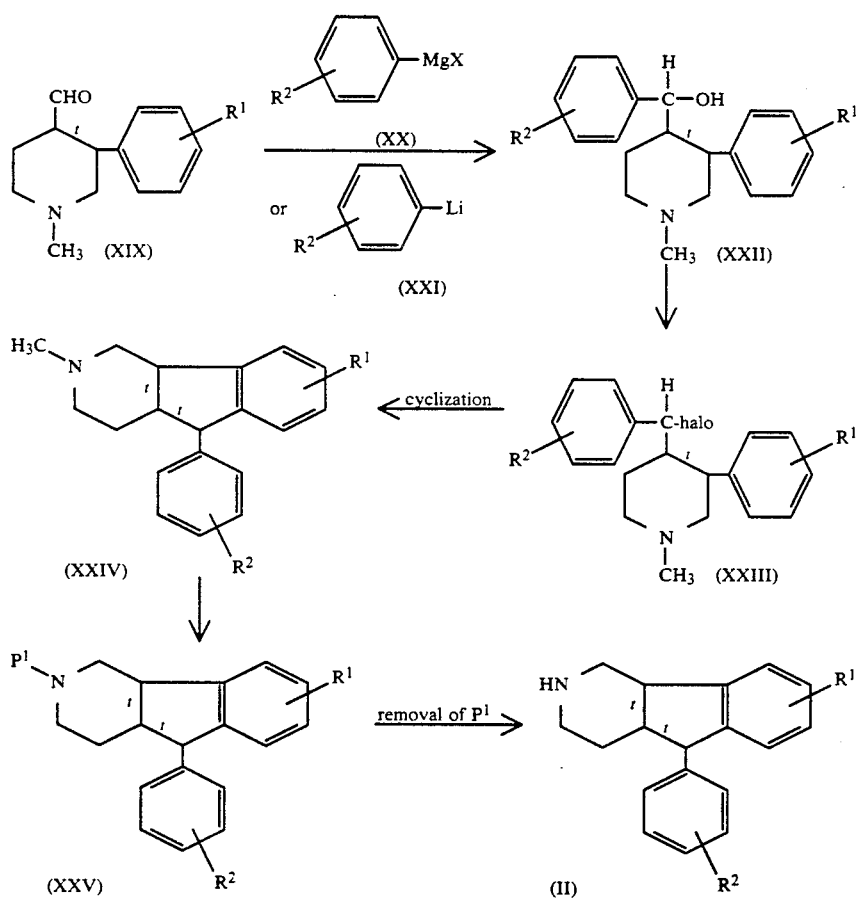

The alcohol intermediate of formula (XXII) is obtained as a mixture of diastereomers by treating a 4-formylpiperidine derivative of formula (XIX) with an organomagnesium halide (Grignard reagent) of formula (XX) wherein X is halo, e.g. chloro, bromo, iodo and the like, or an organolithium compound of formula (XXI). This reaction can be carried out in a suitable solvent following art-known procedures optionally followed by the separation of any undesired cis isomers.

Suitable solvents for said reaction are ethers, e.g. 1,1'-oxybisethane, tetrahydrofuran and the like.

The alcohol of formula (XXII) is treated with a halogenating reagent, such as, for example, thionyl chloride, phosphorus pentachloride, phosphorus trichloride or phosphorus oxychloride in a suitable reaction-inert solvent, such as an aliphatic or aromatic hydrocarbon, e.g. hexane, benzene, methylbenzene; or a halogenated hydrocarbon, e.g. dichloromethane, trichloromethane, thus yielding the corresponding halogenide, also as a mixture of diastereomers, of formula (XXIII), wherein "halo" represents a halogen atom, preferably chloro or bromo.

The tricyclic intermediate of formula (XXIV) can be obtained by cyclization of intermediate of formula (XXIII) via a Friedel-Crafts alkylation reaction in the presence of a Lewis acid, e.g. aluminum chloride, in a suitable reaction-inert solvent, optionally followed by the separation of any regio and/or cis- undesired isomers. Suitable solvents for use in this reaction comprise aliphatic or aromatic hydrocarbons, e.g. pentane, hexane, cyclohexane, benzene and the like; halogenated hydrocarbons, e.g. dichloromethane, trichloromethane, tetrachloromethane and the like.

The intermediates of formula (XXV), wherein $P^1$ is a protective group, such as $C_{1-4}$alkyloxycarbonyl, benzyloxycarbonyl and the like, can be prepared by a nucleophilic exchange reaction in the intermediate of formula (XXIV) with a suitable reagent such as $C_{1-4}$alkyl carbonochloridate, e.g. ethyl carbonochloridate; benzyl carbonochloridate and the like.

The starting material of formula (II) in turn is prepared by deprotecting the intermediates of formula (XXIII) by hydrolysis with, for example, an acid, e.g. hydrochloric acid, hydrobromic acid, acetic acid and the like or a mixture of such acids; or a base, e.g. sodium hydroxide, potassium hydroxide and the like bases.

The other isomers of formula (II) can alternatively be prepared as described in U.S. Pat. No. 3,678,057.

The intermediates of formula (III) can generally be prepared from the corresponding alcohol of formula (XXVI) upon treatment with a halogenating reagent such as a hydrohalic acid, e.g. hydrochloric or hydrobromic acid; thionyl chloride, phosphorous trichloride, phosphoryl chloride or with a sulfonylhalide such as, for example, methanesulfonylchloride, 4-methylbenzenesulfonylchloride and the like.

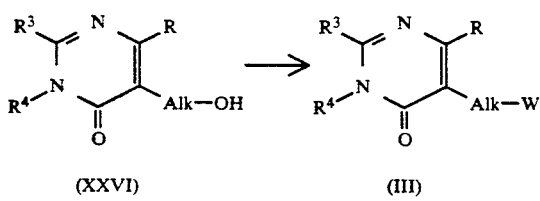

(XXVI)   (III)

The intermediates of formula (XXVI), wherein $R^3$ and $R^4$ taken together form a radical of formula -Z-A-, wherein Z is $NR^5$ and A is $-CR^9=CR^{10}-$ or $-CR^9=N-$, said intermediates being represented by (XXVI-a-1) or (XXVI-a-2) respectively, can be prepared by condensing an appropriately substituted 2-aminoimidazole ($X^1=CR^{10}$) or 2-aminotriazole ($X^1=N$) of formula (XXVII) with an α-acyl-lactone (XXVIII) in the presence of an activating reagent such as a halogenating reagent in a reaction-inert solvent. In some instances the hydroxy group may be converted in situ into a halo group, thus directly yielding an alkylating reagent of formula (III).

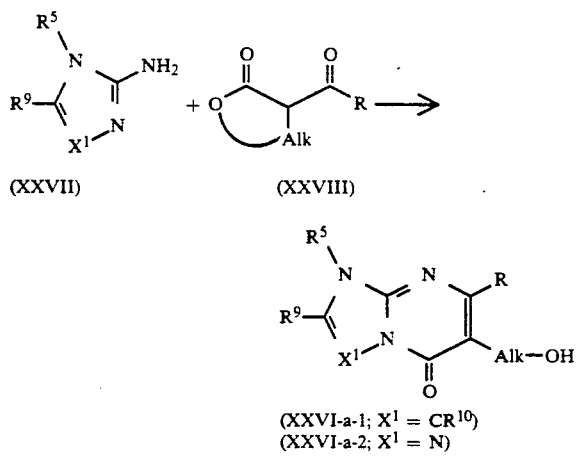

(XXVI-a-1; $X^1 = CR^{10}$)
(XXVI-a-2; $X^1 = N$)

Diastereoisomeric and enantiomeric forms of the compounds may be prepared according to art-known procedures. For example, diastereoisomers may be separated by physical separation methods such as selective crystallization and chromatographic techniques, e.g., counter current distribution, liquid chromatography and the like; and enantiomers may be separated from each other by the selective crystallization of their diastereomeric salts with optically active acids or by chromatographic techniques, e.g. by liquid chromatography using a chiral stationary phase. Pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereoselective methods of preparation. These methods will advantageously employ enantiomerically pure starting materials.

The compounds of formula (I), the pharmaceutically acceptable acid addition salts and stereochemically isomeric forms thereof, are antagonists of neurotransmitters and in particular of the mediator dopamine. Antagonizing said mediator will suppress or relieve a variety of symptoms associated with phenomena induced by the release, in particular the excessive release, of this mediator. Therapeutic indications for using the present compounds are mainly in the CNS area. More particularly dopamine antagonists are reportedly effective in combating psychoses. Furthermore, the present compounds also antagonize serotonin. Combined serotonin-dopamine antagonists are especially interesting as they appear to offer relief of both the positive and negative symptoms of schizophrenia.

The compounds of formula (I) show the additional advantage of being long acting. This can be evidenced, for example, by measuring the plasma levels after oral administration to dogs and by the long acting antiemetic effect exerted by the present compounds on dogs challenged with apomorphine. Hence, the compounds of formula (I) only need to be administered at relatively large intervals, e.g. several days or weeks, the actual time of administration depending on the nature of the compound of formula (I) used and the condition of the subject to be treated. Consequently, the present compounds allow for a more efficient therapy: a reduction in the number of administrations may be expected to result in better compliance of the subject to be treated with the prescribed medication.

In view of their useful pharmacological properties, the subject compounds may be formulated into various pharmaceutical forms for administration purposes. To prepare the pharmaceutical compositions of this invention, an effective amount of the particular compound, in acid addition salt or base form, as the active ingredient is combined in intimate admixture with a pharmaceutically acceptable carrier, which may take a wide variety of forms depending on the form of preparation desired for administration. Such forms comprise tablets (including scored or coated tablets), capsules, pills, powder packets, wafers, injectable solutions or suspensions, teaspoonfuls, tablespoonfuls and the like, and segregated multiples thereof and the like.

In view of the usefulness of the subject compounds in the treatment of diseases associated with the disturbed release of neurotransmitters it is evident that the present invention provides a method of treating warm-blooded animals suffering from such diseases, said method comprising the systemic administration of an amount of a compound of formula (I) or a pharmaceutically acceptable acid addition salt thereof, effective in treating diseases associated with the disturbed release of neurotransmitters. Those of skill in the treatment of such diseases could easily determine the effective amount from the test results presented hereinafter. In general it is contemplated that an effective amount would be from about 0.01 mg/kg to about 4 mg/kg body weight, more preferably from about 0.04 mg/kg to about 2 mg/kg body weight.

The following examples are intended to illustrate and not to limit the scope of the present invention. Unless otherwise stated all parts therein are by weight.

EXPERIMENTAL PART

A. Preparation of Intermediates

Example 1 a) A mixture of 26.53 parts of trans-ethyl 3-(3-fluorophenyl)-1-methyl-4-piperidinecarboxylate: cis-ethyl 3-(3-fluorophenyl)-1-methyl-4-piperidinecarboxylate (40:60), 6.52 parts of potassium hydroxide and 80 parts of methanol was stirred for 3 hours at reflux temperature. After the addition of 78 parts of 2-propanol, the reaction mixture was treated with charcoal. The whole was filtered and the filtrate was evaporated to near dryness in vacuo. The residue was treated with 7.2 parts of water and then diluted with ~210 parts of 1,1'-oxybisethane (to near cloud point). After cooling, the crystallized product was filtered off, washed with 1,1'-oxybisethane and recrystallized twice from a mixture of a minimal amount of damp 2-propanol and 1,1'-oxybisethane, yielding 26.1 parts (75%) of potassium (±)-trans-3-(3-fluorophenyl)-1-methyl-4-piperidinecarboxylate tetrahydrate; mp. 75.2° C. (interm. 1).

b) 91 Parts of intermediate 1 were treated portionwise with 336 parts of thionyl chloride (4×84 parts). Upon completion, the reaction mixture was refluxed for 30 minutes and 200 parts of hexane were added while stirring. After cooling, the hexane layer, containing excess thionyl chloride, was decanted. The precipitated product was washed twice with 200 parts of hexane, yielding 76.55 parts (100%) of (±)-trans-3-(3-fluorophenyl)-1-methyl-4-piperidinecarbonyl chloride hydrochloride (interm. 2).

c) Through a stirred and ice-cooled mixture of 76.55 parts of intermediate 2 and 400 parts of dichloromethane was bubbled an excess of N-methylmethanamine. After stirring for 30 minutes, the product was treated with 360 parts of dichloromethane. The solution was washed twice with 300 parts of water and the combined water layers were extracted twice with 65 parts of dichloromethane. The combined dichloromethane layers were dried (potassium carbonate), filtered and evaporated in vacuo. The residue was taken up in hot n-hexane (+charcoal). The whole was filtered hot and concentrated on a steam bath. The concentrate was recrystallized from n-hexane, yielding 56.1 parts (81%) of (±)-trans-3-(3-fluorophenyl)-N,N,1-trimethyl-4-piperidinecarboxamide, mp. 101.0° C. (interm. 3).

d) To 1675 ml of a lithium aluminum hydride solution 1M in 1,1'-oxybisethane was added dropwise a mixture of 226.9 parts of ethyl acetate in 284 parts of 1,1'-oxybisethane during 3 hours while stirring and cooling in an ice bath (0°–5° C.) and under argon atmosphere. Upon complete addition, stirring was continued for 1 hour. After cooling to −30° C., a solution of 295.2 parts of intermediate 3 in 890 parts of tetrahydrofuran was added rapidly over 5 minutes. The reaction temperature was allowed to rise to −5° to −10° C. and stirring was continued for 4 hours. The reaction mixture was cooled again to −20° C. and then quenched with 64 parts of water, 64 parts of a sodium hydroxide solution 3N and 192 parts of water. The precipitate was filtered off and the organic layer was dried, filtered and evaporated in vacuo, yielding 233.6 parts (95%) of a mixture comprised mostly of (±)-trans-3-(3-fluorophenyl)-1-methyl-4-piperidinecarboxaldehyde (~80%) as a residue (interm. 4).

e) 4-Fluorophenylmagnesium bromide was prepared from a solution of 44.9 parts of magnesium and 356 parts of 4-fluorophenyl bromide in 980 parts of tetrahydrofuran. After cooling in an ice bath (−10° to −15° C.), a solution of 233.6 parts of intermediate 4 in 360 parts of tetrahydrofuran was added dropwise during 4.5 hours. Upon completion, stirring was continued for 15 minutes. The reaction mixture was quenched with a saturated ammonium chloride solution. The separated aqueous layer was extracted with a mixture of 1,1'-oxybisethane and tetrahydrofuran. The combined organic layers were washed twice with a saturated sodium chloride solution, dried, filtered and evaporated in vacuo. The residue was crystallized from 2-propanone, yielding 198 parts (58.9%) of one diastereomer, (±)-(trans,A)-3-(3-fluorophenyl)-α-(4-fluorophenyl)-1-methyl-4-piperidinemethanol; mp. 207.2° C. (interm. 5a). The 2-propanone layer was evaporated and the residue was treated with acetonitrile to give 60.8 parts (18.1%) of the other diastereomer, (±)-(trans,B)-3-(3-fluorophenyl)-α-(4-fluorophenyl)-1-methyl-4-piperidinemethanol (interm. 5b). Both intermediates (5a and 5b) were combined.

f) 162 Parts of thionyl chloride were added to 100.5 parts of a mixture of intermediate 5a and 5b over 45 minutes. Upon complete addition, the reaction mixture was stirred for 1 hour at room temperature and triturated with 125 parts of pentane. The crystallized product was filtered off, washed with pentane and dried, yielding 118 parts (100%) of (±)-trans-4-[chloro(4-fluorophenyl)methyl]-3-(3-fluorophenyl)-1-methylpiperidine hydrochloride as a mixture of diastereomers (interm. 6).

g) To 1040 parts of dichloromethane were added 74 parts of aluminum chloride while cooling (−50° C.) followed by the portionwise addition of 118 parts of intermediate 6. After the reaction has slowly warmed to ~0° C., the whole was poured into a solution of crushed ice, treated with sodium hydroxide. The separated aqueous layer was extracted with dichloromethane. The combined organic layers were dried, filtered and evaporated in vacuo. The residue was taken up in 1,1′-oxybisethane (+activated charcoal). The charcoal was filtered off and the filtrate was evaporated in vacuo. The residue was dissolved in 2-propanone and treated with 4-methylbenzenesulfonate. The salt was filtered off and crystallized twice from hot 2-propanone, yielding 40% (±)-(4aα,5α,9bβ)-8-fluoro-5-(4-fluorophenyl)-1,3,4,4a,5,9b-hexahydro-2-methyl-2H-indeno[1,2-c]-pyridine4-methylbenzenesulfonate(1:1); mp. 217.8° C. (interm. 7).

h) To a stirred solution of 3.2 parts of intermediate 7 in 65 parts of dichloroethane was added dropwise a solution of 3.26 parts of ethyl carbonochloridate in dichloroethane during 1 hour. Upon complete addition, stirring was continued overnight at reflux temperature. The reaction mixture was diluted with 1,1′-oxybisethane and the whole was washed successively with diluted ammonium hydroxide (twice), a hydrochloric acid solution 3N, water and saturated sodium chloride. The separated organic layer was dried, filtered and evaporated in vacuo. The residue was triturated with hexane, yielding 2.7 parts (75.5%) of (±)-(4aα,5α,9bβ)-ethyl 8-fluoro-5-(4-fluorophenyl)-1,3,4,4a,5,9b-hexahydro-2H-indeno[1,2-c]pyridine-2-carboxylate; mp. 111.3° C. (interm. 8)

i) A mixture of 10.7 parts of intermediate 8, 75 parts of hydrobromic acid and 25 parts of acetic acid was stirred at reflux temperature under argon atmosphere. After cooling in an ice bath, the reaction mixture was diluted with 100 parts of water. The precipitated product was filtered off and recrystallized twice from methanol and water, yielding 95% (±)-(4aα,5α,9bβ)-8-fluoro-5-(4-fluorophenyl)-2,3,4,4a,5,9b-hexahydro-1H-indeno[1,2-c]pyridine hydrobromide hemihydrate; mp. 170.1° C. (interm. 9).

Example 2 a) A solution of 4.3 parts of intermediate 9 and 2.29 parts of (S)-(+)-α-hydroxybenzene-acetic acid in 160 parts of acetonitrile was stirred for 1 hour. The precipitated product was filtered off and the filtrate was allowed to stand for 2.5 days to collect a second crop. The combined products were recrystallized twice from 96 parts of acetonitrile, yielding (−)-(4aα,5α,9bβ)-8-fluoro-5-(4-fluorophenyl)-2,3,4,4a,5,9b-hexahydro-1H-indeno[1,2-c]pyridine (S)-α-hydroxybenzeneacetate (1:1) (interm. 10).

b) 2.4 Parts of intermediate 10 were partitioned between 65 parts of dichloromethane and 50 parts of a sodium hydroxide solution 3N. The separated aqueous layer was extracted with dichloromethane. The combined organic layers were dried, filtered and evaporated in vacuo, yielding 1.6 parts (100%) of (−)-(4aα,5α,9bβ)-8-fluoro-5-(4-fluorophenyl)-2,3,4,4a,5,9b-hexahydro-1H-indeno[1,2-c]pyridine as a clear oil (interm. 11).

c) In a similar manner but starting from (R)-(−)-α-hydroxybenzeneacetic acid, there was also prepared: (+)-(4aα,5α,9bβ)-8-fluoro-5-(4-fluorophenyl)-2,3,4,4a,5,9b-hexahydro-1H-indeno[1,2-c]pyridine (interm. 12).

B. Preparation of Final Compounds

Example 3

A solution of 1.5 parts of intermediate 11, 1.7 parts of 3-(2-chloroethyl)-6,7,8,9-tetrahydro-2-methyl-4H-pyrido[1,2-a]pyrimidin-4-one, 0.58 parts of sodium carbonate and 0.87 parts potassium iodide in 15.4 parts of N-methylpyrrolidinone was stirred for 90 minutes at 90°–100° C. The reaction mixture was poured into crushed ice and the separated aqueous layer was extracted twice with 1,1′-oxybisethane. The combined extracts were washed with water, dried, filtered and evaporated in vacuo. The residue was converted into the (E)-2-butenedioate salt in 2-propanol. The salt was filtered off and recrystallized from methanol, yielding 1.81 parts (57.7%) of (−)-(4aα,5α,9bβ)-3-[2-[8-fluoro-5-(4-fluorophenyl)-1,3,4,4a,5,9b-hexahydro-2H-indeno[1,2-c]pyridin-2-yl]ethyl]-6,7,8,9-tetrahydro-2-methyl-4H-pyrido[1,2-a]pyrimidin-4-one (E)-2-butenedioate (1:1); mp. 246.6° C. (compound 1).

Compounds 2–9 listed in Table I were prepared in a similar way.

TABLE 1

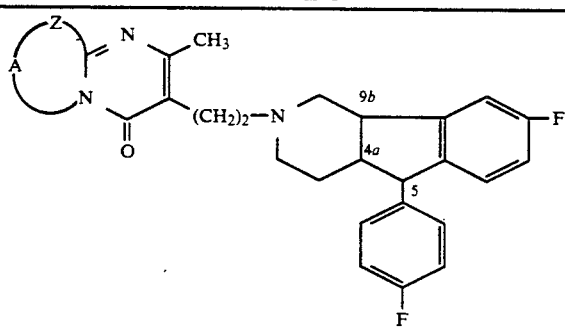

| Comp. No. | —Z—A— | mp./physical data |
|---|---|---|
| 1 | —(CH₂)₄— | 246.6° C./(−)-(4aα,5α,9bβ)/(E)-2-butenedioate (1:1) |
| 2 | —(CH₂)₄— | 237.4° C./(±)-(4aα,5α,9bβ)/(E)-2-butenedioate (1:1) |
| 3 | —N(CH₃)—CH=CH— | 262.0° C./(4aα,5α,9bβ)/2HCl |
| 4 | —S—CH=CH— | 94.0° C./(4aα,5α,9bβ) |
| 5 | —S—(CH₂)₂— | >300° C./(4aα,5α,9bβ)/2HCl |
| 6 | —CH=CH—CH=CH— | 172.9° C./(4aα,5α,9bβ) |

TABLE 1-continued

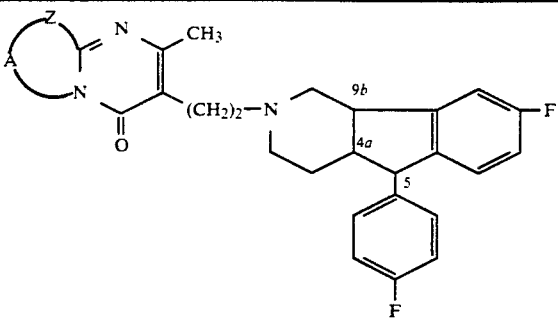

| Comp. No. | —Z—A— | mp./physical data |
|---|---|---|
| 7 | —(CH$_2$)$_2$—CH(CH$_3$)—CH$_2$— | 220.8° C./(4aα,5α,9bβ)/(E)-2-butenedioate (1:1) |
| 8 | —N(CH$_3$)—(CH$_2$)$_2$— | 295.8° C./(4aα,5α,9bβ)/2HCl |
| 9 | —(CH$_2$)$_4$— | 244.8° C./(+)-(4aα,5α,9bβ)/(E)-2-butenedioate (1:1) |

C. Pharmacological examples

The activity of the subject compounds as antipsychotic agents is evidenced by the experimental data obtained in at least one of two different test procedures, viz., the combined apomorphine-, tryptamine- and norepinephrine tests in rats and the apomorphine test in dogs. The tests are carried out following the procedures described hereafter.

Example 4

The Combined Apomorphine (APO)-, Tryptamine (TRY)- and Norepinephrine (NOR) Test in Rats The experimental animals used in this test were adult male Wistar rats (weight 240±10 g). After an overnight fast, the animals were treated subcutaneously or orally with an aqueous solution of the compound under investigation (1 ml/100 g body weight) (time=zero) and put in isolated observation cages. Thirty minutes thereafter (time=30 minutes) 1.25 mg/kg of apomorphine hydrochloride (APO) was injected intravenously and the rats were observed over a 1 hour period for the presence or absence of the following apomorphine-induced phenomena: agitation and stereotypic chewing. At the end of this 1 hour period (time=90 minutes) the same animals were injected intravenously with 40 mg/kg of tryptamine (TRY) and the presence of the typical tryptamine-induced bilateral tonic seizures and hyperaemia of the ears was noted. Two hours after pretreatment (time=120 minutes) finally, the same animals were challenged with 1.25 mg/kg intravenously of norephinephrine (NOR) and possible mortality was looked for up to 60 minutes later.

For compound 1, the ED$_{50}$-value (in mg/kg) being the dose which protects 50% of the animals from apomorphine-, tryptamine- or norepinephrine-induced phenomena was found to be 0.12 (APO), 0.5 (TRY-convulsions), 0.03 (TRY-hyperaemia) and 0.5 (NOR).

The Apomorphine Test in Dogs (APO-dog)

The method used is described by P. A. J. Janssen and C. J. E. Niemegeers in Arzneim.-Forsch. (Drug Res.), 9, 765–767 (1959). Compound 1 was administered subcutaneously or orally to beagle dogs at different doses and the animals were challenged one hour thereafter with a standard dose of 0.31 mg/kg (s.c.) of apomorphine.

The ED$_{50}$ value representing the dose which protects 50% of the animals from emesis, was found to be 0.01 mg/kg for compound 1 and the duration of the effect to last 10 days.

I claim:

1. A chemical compound having the formula:

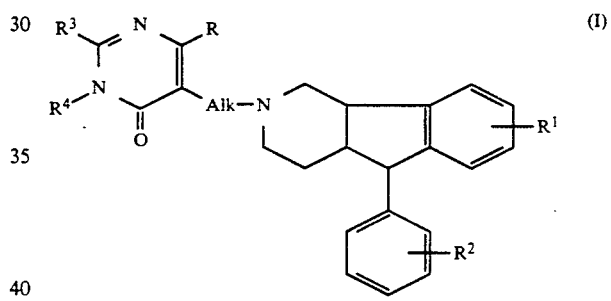

an acid addition salt thereof or a stereochemically isomeric form thereof, wherein R represents hydrogen or C$_{1-6}$alkyl;

R$^1$ and R$^2$ each independently represent hydrogen, halo, hydroxy, C$_{1-6}$alkyloxy, C$_{1-6}$alkyl, trifluoromethyl, mercapto or C$_{1-6}$alkylthio; and R$^3$ represents NR$^5$R$^6$ wherein:
  R$^5$ represents hydrogen or C$_{1-6}$alkyl; and
  R$^6$ represents hydrogen, C$_{1-6}$alkyl, arylC$_{1-6}$alkyl or C$_{1-6}$alkylcarbonyl;

R$^4$ represents hydrogen or C$_{1-6}$alkyl; or

R$^3$ and R$^4$ taken together may form a bivalent radical of formula -Z-A- wherein:

Z is —S—, —NR$^5$—, —CR$^7$=CR$^8$— or —CH$_2$— wherein in the latter one hydrogen atom may be replaced by hydroxy or C$_{1-6}$alkyl and R$^5$ is as defined above and R$^7$ and R$^8$ each independently represent hydrogen or C$_{1-6}$alkyl;

A is a bivalent radical —CR$^9$=CR$^{10}$—, —CH$_2$—CH$_2$— or —CH$_2$—CH$_2$—CH$_2$— wherein in the latter two radicals one or two hydrogen atoms may be replaced by C$_{1-6}$alkyl; and R$^9$ and R$^{10}$ each independently represent hydrogen or C$_{1-6}$alkyl; or when Z is —S— or —NR$^5$—, then A may also be —CR$^{11}$=N—, wherein R$^{11}$ represents hydrogen, C$_{1-6}$alkyl or trifluoromethyl;

Alk represents C$_{1-4}$alkanediyl; and each aryl independently is phenyl optionally substituted with 1, 2 or 3 substituents each independently selected from halo, $C_{1-6}$alkyl, trifluoromethyl, $C_{1-6}$alkyloxy and hydroxy.

2. A chemical compound according to claim 1 wherein the configuration of the 9b and 4a hydrogen atoms and of the 4a and 5 hydrogen atoms is trans.

3. An antipsychotic composition comprising a pharmaceutically acceptable carrier and as active ingredient an antipsychotically effective amount of a compound of formula (I) as claimed in claim 1.

4. An antipsychotic composition according to claim 3 wherein the configuration of the 9b and 4a hydrogen atoms and of the 4a and 5 hydrogen atoms is trans.

5. A method of treating warm-blooded animals suffering from psychotic diseases comprising the administration to said warm-blooded animals of an antipsychotically effective amount of a chemical compound as claimed in claim 1.

6. A method according to claim 5 wherein the configuration of the 9b and 4a hydrogen atoms and of the 4a and 5 hydrogen atoms is trans.

* * * * *